(12) United States Patent
Peters et al.

(10) Patent No.: US 7,612,074 B2
(45) Date of Patent: Nov. 3, 2009

(54) DIAZABICYCLIC ARYL DERIVATIVES AS CHOLINERGY LIGANDS

(75) Inventors: Dan Peters, Balleup (DK); Daniel B. Timmermann, Ballerup (DK); Gunnar M. Olsen, Ballerup (DK); Elsebet Østergaard Nielsen, Ballerup (DK); Tino Dyhring Jørgensen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 67 days.

(21) Appl. No.: 11/663,967

(22) PCT Filed: Nov. 29, 2005

(86) PCT No.: PCT/EP2005/056300

§ 371 (c)(1),
(2), (4) Date: Mar. 28, 2007

(87) PCT Pub. No.: WO2006/058879

PCT Pub. Date: Jun. 8, 2006

(65) Prior Publication Data

US 2007/0265271 A1   Nov. 15, 2007

(30) Foreign Application Priority Data

Nov. 30, 2004 (DK) ............................... 2004 01863

(51) Int. Cl.
*A61K 31/497* (2006.01)
(52) U.S. Cl. ................. 514/252.1; 544/336; 549/505
(58) Field of Classification Search ............. 514/252.1; 544/336; 549/505
See application file for complete search history.

(56) References Cited

U.S. PATENT DOCUMENTS

| 3,293,251 A | 12/1966 | Cignarella et al. |
| 3,328,396 A | 6/1967 | Kirchner |
| 2003/0225268 A1 | 12/2003 | Bunnelle et al. |
| 2005/0250808 A1 | 11/2005 | Xie et al. |

FOREIGN PATENT DOCUMENTS

| BE | 618 813 A | 10/1962 |
| BE | 633 541 A | 10/1963 |
| WO | WO 95/23152 | * 8/1995 |
| WO | WO-2004/016616 A1 | 2/2004 |
| WO | WO-2004/043960 A1 | 5/2004 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Cignarella, et al. J. Med. Chem., 6, 1, 1963, pp. 29-36.*
Patani, et al. Chem. Rev., 96, 1996, pp. 3147-3176.*
Villa et al., European Journal of Medicinal Chemistry, vol. 36, No. 6, Jun. 2001, pp. 495-506.
Cignarella et al., Farmaco, vol. 53 (10,11), pp. 667-674, 1998.
Fontanella et al., Farmaco, Edizione Scientifica, vol. 30(9), pp. 742-753, (1975).

* cited by examiner

*Primary Examiner*—James O Wilson
*Assistant Examiner*—Douglas M Willis
(74) *Attorney, Agent, or Firm*—Birch, Stewart, Kolasch & Birch, LLP

(57) ABSTRACT

This invention relates to novel diazabicyclic aryl compounds of the formula

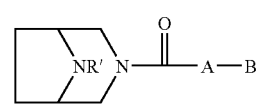

(I)

wherein: R' represents hydrogen or alkyl; A represents an aromatic monocyclic or bicyclic carbocyclic or heterocyclic; and is hydrogen or a subsituent as defined in the specification. The compounds are cholinergic ligands at the nicotinic acetylcholine receptors and modulators of the monoamine receptors and transporters. The compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

5 Claims, No Drawings

DIAZABICYCLIC ARYL DERIVATIVES AS CHOLINERGY LIGANDS

FIELD OF THE INVENTION

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

DESCRIPTION OF RELEATED ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

BRIEF SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic aryl derivatives of Formula I

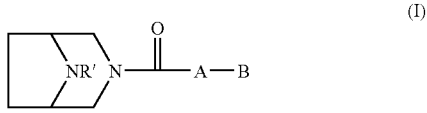

any of its enantiomers or any mixture of its enantiomers, or a pharmaceutically acceptable salt thereof, wherein
R' represents hydrogen or alkyl;
A represents an aromatic monocyclic or bicyclic carbocyclic or heterocyclic group; and
B represents hydrogen, alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido or N-alkyl-ureido, or an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido and N-alkyl-ureido.

In its second aspect the invention provides pharmaceutical compositions comprising a therapeutically effective amount of the diazabicyclic aryl derivative of the invention, or a pharmaceutically-acceptable addition salt thereof, together with at least one pharmaceutically-acceptable carrier or diluent.

In a further aspect the invention relates to the use of the diazabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicyclic aryl derivative of the invention.

Other objects of the invention will be apparent to the person skilled in the art from the following detailed description and examples.

DETAILED DESCRIPTION OF THE INVENTION

Diazabicyclic Aryl Derivatives

In a first aspect novel 3,8-diaza-bicyclo[3.2.1]octane aryl derivatives are provided. The diazabicyclic aryl derivatives of the invention may be represented by the general Formula I

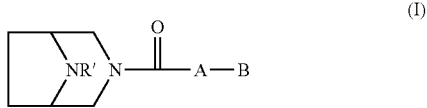

any of its enantiomers or any mixture of its enantiomers, or a pharmaceutically acceptable salt thereof, wherein R' represents hydrogen or alkyl;

A represents an aromatic monocyclic or bicyclic carbocyclic or heterocyclic group; and B represents hydrogen, alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido, or an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido and N,N-dialkyl-sulfonamido.

In a preferred embodiment of the invention R' represents hydrogen or alkyl.

In a more preferred embodiment R' represents alkyl.

In an even more preferred embodiment R' represents methyl or ethyl.

In another preferred embodiment of the invention A represents an aromatic monocyclic or bicyclic carbocyclic or heterocyclic group.

In a more preferred embodiment A represents an aromatic monocyclic group selected from phenyl, furanyl and benzo[b]furanyl.

In an even more preferred embodiment A represents an aromatic monocyclic group selected from phen-1,4-diyl, furan-2,5-diyl and benzo[b]furan-1-yl.

In a still more preferred embodiment A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl and triazinyl.

In a yet more preferred embodiment A represents an aromatic heterocyclic group selected from furanyl, in particular furan-2,3-diyl, furan-2,4-diyl and furan-2,5-diyl; thienyl, in particular thien-2,3-diyl, thien-2,4-diyl and thien-2,5-diyl; pyrrolyl, in particular pyrrol-2,3-diyl, pyrrol-2,4-diyl and pyrrol-2,5-diyl; oxazolyl, in particular oxazol-2,4-diyl and oxazol-2,5-diyl; thiazolyl, in particular thiazol-2,4-diyl and thiazol-2,5-diyl; imidazolyl, in particular imidazol-2,4-diyl and imidazol-2,5-diyl; isoxazolyl, in particular isoxazol-3,4-diyl and isoxazol-3,5-diyl; isothiazolyl, in particular isothiazol-3,4-diyl and isothiazol-3,5-diyl; pyridyl, in particular pyrid-2,4-diyl, pyrid-2,5-diyl and pyrid-2,6-diyl; pyridazinyl, in particular pyridazin-3,5-diyl and pyridazin-3,6-diyl; pyrimidinyl, in particular pyrimidin-2,4-diyl and pyrimidin-2,5-diyl; pyrazinyl in particular pyrazin-2,5-diyl and pyrazin-2,6-diyl.

In a further preferred embodiment A represents furanyl, in particular furan-2,3-diyl, furan-2,4-diyl or furan-2,5-diyl; oxazolyl, in particular oxazol-2,4-diyl or oxazol-2,5-diyl; or isoxazolyl, in particular isoxazol-3,4-diyl or isoxazol-3,5-diyl.

In a still further preferred embodiment A represents furanyl, in particular furan-2,4-diyl or furan-2,5-diyl.

In a still further preferred embodiment A represents an aromatic bicyclic heterocyclic group selected from indolyl, benzo[b]furanyl, benzo[b]thienyl, and benzimidazolyl, and B represents hydrogen.

In a still further preferred embodiment A represents an aromatic bicyclic heterocyclic group selected from indolyl, benzo[b]furanyl, benzo[b]thienyl, and benzimidazolyl, and B represents hydrogen.

In a more preferred embodiment A represents benzo[b]furanyl.

In a third preferred embodiment of the invention B represents hydrogen, alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido, or an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido and N,N-dialkyl-sulfonamido.

In a more preferred embodiment B represents hydrogen, alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido In an even more preferred embodiment B represents phenyl or naphthyl, which carbocyclic aryl groups are optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido and N,N-dialkyl-sulfonamido.

In a yet more preferred embodiment B represents phenyl, which carbocyclic group is optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido and N-alkyl-ureido.

In a still more preferred embodiment B represents phenyl optionally substituted with amino, nitro, alkyl-carbonyl-amino, ureido or N-alkyl-ureido.

In a most preferred embodiment the diazabicyclic aryl derivative of the invention is Furan-2-yl-(8-methyl-3,8-diaza-bicyclo[3.2.1]oct-3-yl)-methanone;

(8-Methyl-3,8-diaza-bicyclo[3.2.1]oct-3-yl)-[5-(4-nitro-phenyl)-furan-2-yl]-methanone;

(8-Methyl-3,8-diaza-bicyclo[3.2.1]oct-3-yl)-[5-(3-trifluoromethyl-phenyl)-furan-2-yl]-methanone;

Benzofuran-2-yl-(8-methyl-3,8-diaza-bicyclo[3.2.1]oct-3-yl)-methanone;

(5-Bromo-furan-2-yl)-(8-methyl-3,8-diaza-bicyclo[3.2.1]oct-3-yl)-methanone;

Biphenyl-4-yl-(8-methyl-3,8-diaza-bicyclo[3.2.1]oct-3-yl)-methanone;

[5-(4-Amino-phenyl)-furan-2-yl]-(8-methyl-3,8-diaza-bicyclo[3.2.1]oct-3-yl)-methanone;

[5-(3-Amino-phenyl)-furan-2-yl]-(8-methyl-3,8-diaza-bicyclo[3.2.1]oct-3-yl)-methanone;

N-{4-[5-(8-Methyl-3,8-diaza-bicyclo[3.2.1]octane-3-carbonyl)-furan-2-yl]-phenyl}-acetamide;

N-{3-[5-(8-Methyl-3,8-diaza-bicyclo[3.2.1]octane-3-carbonyl)-furan-2-yl]-phenyl}-acetamide; or 1-Ethyl-3-{4-[5-(8-methyl-3,8-diaza-bicyclo[3.2.1]octane-3-carbonyl)-furan-2-yl]-phenyl}-urea;

or an enantiomers or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aromatic monocyclic or bicyclic heterocyclic group is a mono- or bicyclic compound, which holds one or more heteroatoms in its ring structure. The term "bi- and poly-heterocyclic groups" includes benzofused five- and six-membered heterocyclic rings containing one or more heteroatoms. Preferred heteroatoms include nitrogen (N), oxygen (O), and sulphur (S).

In the context of this invention a 5-6 membered aromatic monocyclic heterocyclic designates a 5- or 6-membered heteroaryl, which holds one or more heteroatoms in its ring structure. Preferred heteroatoms include nitrogen (N), oxygen (O), and sulphur (S).

Preferred 5 membered heteroaryl groups of the invention include furanyl, in particular furan-2- or 3-yl; thienyl, in particular thien-2- or 3-yl; pyrrolyl(azolyl), in particular pyrrol-2- or 3-yl; oxazolyl, in particular oxazol-2, 4- or 5-yl; thiazolyl, in particular thiazol-2, 4- or 5-yl; isoxazolyl, in particular isoxazol-3, 4- or 5-yl; isothiazolyl, in particular isothiazol-3-, 4- or 5-yl; oxadiazolyl, in particular 1,2,3-oxadiazol-4,5-diyl or 1,3,4-oxadiazol-2,5-diyl and thiadiazolyl, in particular 1,2,3-thiadiazol-4- or 5-yl, or 1,3,4-thiadiazol-2-yl.

More preferred 5 membered heteroaryl groups of the invention include oxadiazolyl, in particular 1,2,3-oxadiazol-4,5-diyl or 1,3,4-oxadiazol-2,5-diyl and thiadiazolyl, in particular 1,2,3-thiadiazol-4- or 5-yl, or 1,3,4-thiadiazol-2-yl.

Preferred 6 membered heteroaryl groups of the invention include pyridyl, in particular pyrid-2-, 3- or 4-yl; and pyrazinyl, in particular pyrazin-2- or 3-yl.

Preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl; and benzothiazolyl, in particular benzothiazol-2-, 5- or 6-yl.

Pharmaceutically Acceptable Salts

The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine-containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a diazabicyclic aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine-containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Diethyl cis-1-methylpyrrolidine-2,5-dicarboxylate (Intermediate Compound)

Diethyl mezo-2,5-dibromoadipate (101.7 g, 0.283 mol) was dissolved by heating under argon in THF (400 ml) and then cooled to 0° C. To the obtained solution a precooled solution of methylamine (27.3 g; 0.88 mol) in THF (150 ml) was added and the mixture was stirred at room temperature for 18 hours. The separated crystalline material was filtered off, the filtrate concentrated and the residue chromatographed on a silica gel column (10 cm long) with hexane-ethyl acetate 4:1 as eluent to afford 58.9 g (91%).

$^1$H NMR (300 MHz, CDCl$_3$): δ 1.15 (t, 6H); 1.9-2.0 (m, 4H); 2.38 (s, 3H); 2.99 (m, 2H); 4.07 (q, 4H). $^{13}$C NMR (75 MHz, CDCl$_3$): δ 13.98; 27.68; 40.82; 60.39; 67.93; 68.06; 172.32.

3-Benzyl-8-methyl-3,8-diazabicyclo[3.2.1]octane-2, 4-dione (Intermediate Compound)

To a solution of diethyl cis-1-methylpyrrolidine-2,5-dicarboxylate (74.8 g; 0.383 mol) in xylene (150 ml) benzylamine (41.0 g; 0.383 mol) was added and the mixture heated to reflux for 16 hours. Then xylene was removed at reduced pressure and the residue was heated at 220° C. for 18 hours. The obtained crude product was distilled by portions (30-40 g) on Büchi oven for distillation at 180° C. and 0.1 mbar, and the first fraction collected (after about 1 hour). The combined first fractions were crystallized from a mixture of hexane and ethyl acetate 1:1 to yield 30.6 (34%).

$^1$H NMR (300 MHz, CDCl$_3$): δ 1.88 (m, 2H); 2.34 (m, 2H); 2.42 (s, 3H); 3.80 (dd, 2H); 4.88 (s, 2H); 7.2-7.4 (m, 5H). $^{13}$C NMR (75 MHz, CDCl$_3$): 26.69; 35.82; 41.26; 65.72; 127.42; 128.36; 128.62; 136.91; 173.26.

3-Benzyl-8-methyl-3,8-diazabicyclo[3.2.1]octane (Intermediate Compound)

To a solution of 3-benzyl-8-methyl-3,8-diazabicyclo [3.2.1]octane-2,4-dione (28.3 g; 0.116 mol) in 200 ml of absolute dioxane LiAlH$_4$ (7.6 g; 0.2 mol) was added and the mixture boiled under argon for 18 hours. Then a mixture of water (7.5 ml) and dioxane (40 ml) was added drop-wise to the reaction mixture. The suspension was mixed for 20 minutes and filtered trough a dense glass filter. The filtrate was evaporated and the residue was distilled on Büchi oven for distillation at 120° C. and 0.1 mbar. Yield 17.6 g (70%).

$^1$H NMR (300 MHz, CDCl$_3$): δ 1.7-1.9 (m, 4H); 2.18 (s, 3H); 2.25 (d, 2H); 2.48 (dd, 2H); 2.95 (m, 2H); 3.39 (s, 2H); 7.1-7.3 (m, 5H).

8-Methyl-3,8-diazabicyclo[3.2.1]octane (Intermediate Compound)

To a degassed by argon solution of 3-benzyl-8-methyl-3, 8-diazabicyclo[3.2.1]octane (17.6 g; 0.08 mol) in methanol (50 ml), 10% Pd/C (1.0 g) was added and hydrogen passed into reaction mixture for 24 hours. The catalyst was filtered off, the filtrate evaporated and the residue distilled on Büchi oven for distillation at 100° C. and 0.1 mbar. Yield 8.5 g (85%).

$^1$H NMR (300 MHz, CDCl$_3$): δ 1.6 (m, 2H); 1.86 (s, 1H); 1.9-2,0 (m, 2H); 2,17 (s, 3H); 2.53 (m, 2H); 2.9-3.0 (m, 4H). $^{13}$C NMR (75 MHz, CDCl$_3$): δ 24.73; 41.72; 52.10; 62.08.

Method A

Furan-2-yl-(8-methyl-3,8-diaza-bicyclo[3.2.1]oct-3-yl)-methanone free base (Compound A1)

A mixture of 2-furoic acid (1.33 g, 11.9 mmol) and thionyl chloride (20 ml) was stirred at reflux for 2 hours. The mixture was evaporated and co-evaporated with toluene, 8-methyl-3, 8-diaza-bicyclo[3.2.1]octane (1.5 g, 11.9 mmol) and 1,2-dimethoxyethane (40 ml) was added and was stirred at room temperature for 15 hours. Aqueous sodium hydroxide (50 ml, 1M) was added and the mixture was extracted twice with dichloromethane (2×40 ml). Chromatography on silica gel with dichloromethane, 10% methanol and 1% aqueous ammonia as solvent gave the title compound as a solid. Mp. 106° C. Yield 1.41 g (54%).

(8-Methyl-3,8-diaza-bicyclo[3.2.1]oct-3-yl)-[5-(4-nitro-phenyl)-furan-2-yl]-methanone free base (Compound A2)

Was prepared according to method A. Mp. 140° C.

(8-Methyl-3,8-diaza-bicyclo[3.2.1]oct-3-yl)-[5-(3-trifluoromethyl-phenyl)-furan-2-yl]-methanone fumaric acid salt (Compound A3)

Was prepared according to method A. Mp. 108.7-109.4° C.

Benzofuran-2-yl-(8-methyl-3,8-diaza-bicyclo[3.2.1] oct-3-yl)-methanone fumaric acid salt (Compound A4)

Was prepared according to method A. Mp. 150-155° C.

(5-Bromo-furan-2-yl)-(8-methyl-3,8-diaza-bicyclo [3.2.1]oct-3-yl)-methanone free base (Compound A5)

Was prepared according to method A. Mp. 101-104° C.

Biphenyl-4-yl-(8-methyl-3,8-diaza-bicyclo[3.2.1] oct-3-yl)-methanone fumaric acid salt (Compound A6)

Was prepared according to method A. Mp. 197-207° C.

Method B

[5-(4-Amino-phenyl)-furan-2-yl]-(8-methyl-3,8-diaza-bicyclo[3.2.1]oct-3-yl)-methanone free base (Compound B1)

A mixture of (8-methyl-3,8-diaza-bicyclo[3.2.1]oct-3-yl)-[5-(4-nitro-phenyl)-furan-2-yl]-methanone free base, palladium on carbon (5%, 0.60 g), ethanol (20 ml) and tetrahydrofuran (20 ml) was stirred under hydrogen (530 ml). The crude mixture was purified by chromatography on silica gel with dichloromethane, 10% methanol and 1% aqueous ammonia as solvent gave the title compound as a solid. Mp. 189.7-191.3° C. Yield 1.68 (65%).

[5-(3-Amino-phenyl)-furan-2-yl]-(8-methyl-3,8-diaza-bicyclo[3.2.1]oct-3-yl)-methanone fumaric acid salt (Compound B2)

Was prepared according to method B. Mp. 171.7° C.

Method C

N-{4-[5-(8-Methyl-3,8-diaza-bicyclo[3.2.1]octane-3-carbonyl)-furan-2-yl]-phenyl}-acetamide fumaric acid salt (Compound C1)

A mixture of [5-(4-amino-phenyl)-furan-2-yl]-(8-methyl-3,8-diaza-bicyclo[3.2.1]oct-3-yl)-methanone (0.40, 1.28 mmol), acetic acid anhydride (197 mg, 1.93 mmol) and dichloromethane (5 ml) was stirred at room temperature for 5 hours. Aqueous sodium hydroxide (5 ml, 1M) was added and the mixture was extracted twice with dichloromethane (2×10 ml). Chromatography on silica gel with dichloromethane, 10% methanol and 1% aqueous ammonia as solvent gave the title compound. The corresponding salt was obtained by addition of a diethyl ether and methanol mixture (9:1) saturated with fumaric acid. Mp. 257-259° C. Yield 515 mg (86%).

N-{3-[5-(8-Methyl-3,8-diaza-bicyclo[3.2.1]octane-3-carbonyl)-furan-2-yl]-phenyl}-acetamide fumaric acid salt (Compound C2)

Was prepared according to method C. Mp. 189-193° C.

Method D

1-Ethyl-3-{4-[5-(8-methyl-3,8-diaza-bicyclo[3.2.1]octane-3-carbonyl)-furan-2-yl]-phenyl}-urea (Compound D1)

To a mixture of [5-(4-amino-phenyl)-furan-2-yl]-(8-methyl-3,8-diaza-bicyclo[3.2.1]oct-3-yl)-methanone (0.44 g, 1.41 mmol) and methanol (30 ml) was added: ethylisocyanate (291 mg, 4.08 mmol) at −50° C. and then allowed to reach room temperature. Aqueous sodium hydroxide (5 ml, 1M) was added and the mixture was extracted twice with dichloromethane (2×10 ml). Chromatography on silica gel with dichloromethane, 10% methanol and 1% aqueous ammonia as solvent gave the title compound. Yield 519 mg (96%). The corresponding salt was obtained by addition of a diethyl ether and methanol mixture (9:1) saturated with fumaric acid. Mp. 183.6-186.4° C.

The invention claimed is:

1. A diazabicyclic aryl compound represented by Formula (I)

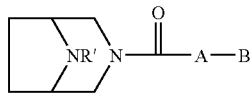

any of its enantiomers or diastereomers, or a pharmaceutically acceptable salt thereof, wherein
R' represents hydrogen or alkyl;
A represents a furanyl group; and
B represents phenyl, which phenyl is optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, and N-alkyl-ureido.

2. The diazabicyclic aryl compound of claim 1, any of its enantiomers or diastereomers, or a pharmaceutically acceptable salt thereof, wherein R' represents alkyl.

3. The diazabicyclic aryl compound of claim 1, any of its enantiomers or diastereomers, or a pharmaceutically acceptable salt thereof, wherein B represents phenyl optionally substituted with amino, nitro, alkyl-carbonyl-amino, ureido, or N-alkyl-ureido.

4. The diazabicyclic aryl compound of claim 1, which is
(8-Methyl-3,8-diaza-bicyclo[3.2.1]oct-3-yl)-[5-(4-nitrophenyl)-furan-2-yl]-methanone;
(8-Methyl-3,8-diaza-bicyclo[3.2.1]oct-3-yl)-[5-(3-trifluoromethyl-phenyl)-furan-2-yl]-methanone;
[5-(4-Amino-phenyl)-furan-2-yl]-(8-methyl-3,8-diaza-bicyclo[3.2.1]oct-3-yl)-methanone;
[5-(3-Amino-phenyl)-furan-2-yl]-(8-methyl-3,8-diaza-bicyclo[3.2.1]oct-3-yl)-methanone;
N-{4-[5-(8-Methyl-3,8-diaza-bicyclo[3.2.1]octane-3-carbonyl)-furan-2-yl]-phenyl}-acetamide;
N-{3-[5-(8-Methyl-3,8-diaza-bicyclo[3.2.1]octane-3-carbonyl)-furan-2-yl]-phenyl}-acetamide; or
1-Ethyl-3-{4-[5-(8-methyl-3,8-diaza-bicyclo[3.2.1]octane-3-carbonyl)-furan-2-yl]-phenyl}-urea;
or an enantiomer or a diastereomer, or a pharmaceutically acceptable salt thereof.

5. A pharmaceutical composition comprising a therapeutically effective amount of a diazabicyclic aryl compound of claim 1, or an enantiomer or a diastereomers, or a pharmaceutically-acceptable salt thereof, together with at least one pharmaceutically-acceptable carrier or diluent.

* * * * *